United States Patent [19]
Bozzacco

[11] Patent Number: 5,908,613
[45] Date of Patent: Jun. 1, 1999

[54] COMPOSITION FOR THE TREATMENT AND PREVENTION OF PERIODONTAL DISEASE

[76] Inventor: Craig Bozzacco, 7866 Spring Ave., Elkins Park, Pa. 19027

[21] Appl. No.: 08/924,988

[22] Filed: Sep. 8, 1997

[51] Int. Cl.$^6$ .............................. A61K 7/16; A61K 7/26; A61K 35/78; A61K 38/43
[52] U.S. Cl. .......................... 424/50; 424/58; 424/195.1; 514/690
[58] Field of Search ........................ 514/690; 424/49–88

[56] References Cited

U.S. PATENT DOCUMENTS

| | | | |
|---|---|---|---|
| 4,654,373 | 3/1987 | Bertelli | 514/690 |
| 4,925,655 | 5/1990 | Smigel et al. | 424/52 |
| 5,378,461 | 1/1995 | Neigut | 424/94.1 |
| 5,472,684 | 12/1995 | Nabi et al. | 424/49 |

OTHER PUBLICATIONS

Hankioka et al Molecular Aspects of Medicine (1994) 15/Suppl S–241–S243 1994 Topical Application of Coenzyme Q10 to The Periodontal Pocket.

Shizukushi et al Biomed. Res (4)(1): 33–40 Effect of Coenzyme Q10 on Experimental Periodontitis in Dogs, 1983.

*Primary Examiner*—Shep K. Rose
*Attorney, Agent, or Firm*—LaMorte & Associates

[57] ABSTRACT

The present invention is a compound and method for treating and preventing periodontal disease. The compound contains a gum tissue regeneration agent, such as coenzyme $Q_{10}$, and a antimicrobial agent, such as melaleuca alternifolia extract oil, mixed into a solution medium. The compound is applied to the bristles of a brush. The brush then is used to introduce the compound into any pockets that may exist between and around the teeth and gums because of periodontal disease. Once introduced into pockets between the teeth and gums, the compound has a dual effect. First, the antimicrobial agent kills any bacteria in the pockets and prevents the growth of new bacteria in the pockets. Second, the gum tissue regeneration agent promotes growth of the gums against the teeth. As a result, the size of the pockets is reduced over time until the pockets are no longer abnormal and the damage from past periodontal disease is at least partially repaired.

7 Claims, 1 Drawing Sheet

5,908,613

COMPOSITION FOR THE TREATMENT AND PREVENTION OF PERIODONTAL DISEASE

BACKGROUND OF THE INVENTION

1. Field of the Invention

In general, the present invention relates to topical treatments that are used in treating and preventing periodontal disease. More particularly, the present invention relates to compositions that are applied in pockets in between the tooth and gum to heal past damage caused by periodontal disease.

2. Description of the Prior Art

Periodontal disease accounts for more lost teeth in adults than any other cause. Periodontal disease begins with plaque bacteria in the mouth. As plaque bacteria digest food, the by-products given off by the bacteria irritate the gums. As a result, the gums often become red, tender, swollen and exhibit a tendency to bleed. If left untreated, the tissue that attaches the gums to the teeth is eventually destroyed by the irritants produced by the plaque bacteria. This causes the gums to begin to pull away from the teeth. As the gums pull away from the teeth, pockets are created that harbor yet more bacteria. The pockets therefore become ever larger as the cycle repeats. Eventually, the amount of gum loss is so large that the tooth is lost.

In treating gum disease, two approaches can be taken. The most common approach is to kill the plaque bacteria by practicing good dental hygiene. The prior art is replete with different toothpastes and mouth rinses that are designed to kill plaque bacteria during a dental hygiene regimen. Good dental hygiene using such prior art preparations will retard the spread of periodontal disease but will not actively repair the damage to the gums that has already occurred.

A second less common approach to treating periodontal disease is to strengthen the ability of the gum tissue to resist the encroachment of the plaque bacteria and the disease it causes. One composition used in this approach has been coenzyme $Q_{10}$. Coenzyme $Q_{10}$ has its chemical name 2,3-dimethoxy-5-methyl-6-decaprenyl-benzoquinone. Coenzyme $Q_{10}$ can be produced in different ways but it is most commonly produced by cultivating a microorganism of genus Aureobasidium or Trichosporon in a culture medium containing a large quantity of p-hydroxy benzoic acid. Such a method of Coenzyme $Q_{10}$ production is described in U.S. Pat. No. 4,367,288 to Kaneko, entitled Method For Producing Coenzyme $Q_{10}$.

As is discussed in U.S. Pat. No. 4,654,373 to Bertelli and the book The Miracle Nutrient Coenzyme $Q_{10}$, by Bliznakov et al., coenzyme $Q_{10}$ has the ability to generate regrowth of damaged gum tissue when topically applied to the gum tissue. The only problem associated with coenzyme $Q_{10}$ is that it does not kill the plaque bacteria effecting the gums. Rather, the coenzyme $Q_{10}$ only enhances the ability of the gum tissue to resist the adverse effects of the plaque bacteria.

A need therefore exists in the art for a treatment for periodontal disease that both actively kills plaque bacteria and actively promotes gum tissue regeneration. Such a composition would therefore both prevent the development of periodontal disease and promote the healing of damage caused by past periodontal disease. This need is provided for by the present invention as set forth in the below description and claims.

SUMMARY OF THE INVENTION

The present invention is a compound and method for treating and preventing periodontal disease. The compound contains a gum tissue regeneration agent, such as coenzyme $Q_{10}$, and a antimicrobial agent, such as melaleuca alternifolia extract oil, mixed into a solution medium. The compound is applied to the bristles of a brush. The brush then is used to introduce the compound into any pockets that may exist in between the teeth and gums because of periodontal disease. Once introduced into pockets between the teeth and gums, the compound has a dual effect. First, the antimicrobial agent kills any bacteria in the pockets and prevents the growth of new bacteria in the pockets. Second, the gum tissue regeneration agent promotes growth of the gums against the teeth. As a result, the size of the pockets is reduced over time until the pockets are no longer abnormal and the damage from past periodontal disease is at least partially repaired.

BRIEF DESCRIPTION OF THE DRAWINGS

For a better understanding of the present invention, reference is made to the following description of an exemplary embodiment thereof, considered in conjunction with the accompanying drawing, in which.

DETAILED DESCRIPTION OF THE INVENTION

The present invention is a composition that includes an antimicrobial agent, a gum regeneration agent and solution medium. The composition is manually applied to the gum line in between the teeth and gums so that the composition fills any gaps present in between the teeth and gums. Once present within any gap, the antimicrobial agent kills any plaque bacterial present while the gum regeneration agent promotes the regrowth of the gum tissue onto the teeth. Treatments are repeated until any abnormal gaps between the teeth and the gums have healed.

In the present invention composition, the gum regeneration material is preferably coenzyme $Q_{10}$. As has been previously indicated, coenzyme $Q_{10}$ has the ability to promote the regrowth of gum tissue onto the teeth even after experiencing damage from periodontal disease.

The antimicrobial agent is preferably an extract oil of the plant species Melaleuca Alternifolia. The melaleuca alternifolia is a shrub-like tree that is indigenous to the swampy north costal regions of Australia. The British Pharmaceutical Codex of 1949 lists melaleuca alternifolia as Oleum Melaleuca consisting of terpinenes, cymene, pinene, 1-trepinene-ol, cineole, sequiterpenes and sesquiterpene alcohols. Extract oil of melaleuca alternifolia is an oil that is extracted using a steam distillation technique. One kilogram of foliage typically produces between 12 grams and 25 grams of extract oil after distillation. Various compositions containing the extract oil, commonly known as tea tree oil, have been used as a topical medication for over a century. Currently, there are United States patents that use compositions containing melaleuca alternifolia extract oil for the treatment of sunburn, genital herpes, and flea infestation. Patents showing compounds containing melaleuca alternifolia extract oil are also used as topical muscle relaxers and as antiperspirants.

In the present invention composition, melaleuca alternifolia extract oil can be present in concentrations between 0.02% and 75% by volume. However, the melaleuca alternifolia extract oil preferably is present in concentrations between 0.33 ml and 1.5 ml per fluid ounce. The coenzyme $Q_{10}$ is present in concentrations between 0.05% and 75% by weight. However, in the preferred composition, the coenzyme $Q_{10}$ is present in concentrations of between 200 mg and 1000 mg per ounce. The remainder of the composition consists of the solution medium. The solution medium is preferably a vegetable oil such as olive oil, corn oil or the like. The melaleuca alternifolia extract oil readily mixes with such vegetable oils. The coenzyme $Q_{10}$ is typically manufactured as a powder. The coenzyme $Q_{10}$ either dissolves in the solution medium or is suspended in the solution medium depending upon what type of oil is selected as the solution medium.

Figure 1:
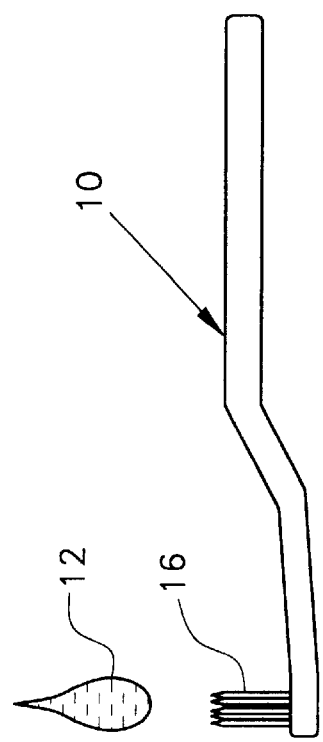
FIG. 1 selectively fragmented view of a mouth with periodontal disease to illustrate a preferred method of using the present invention compound.
Figure 1:
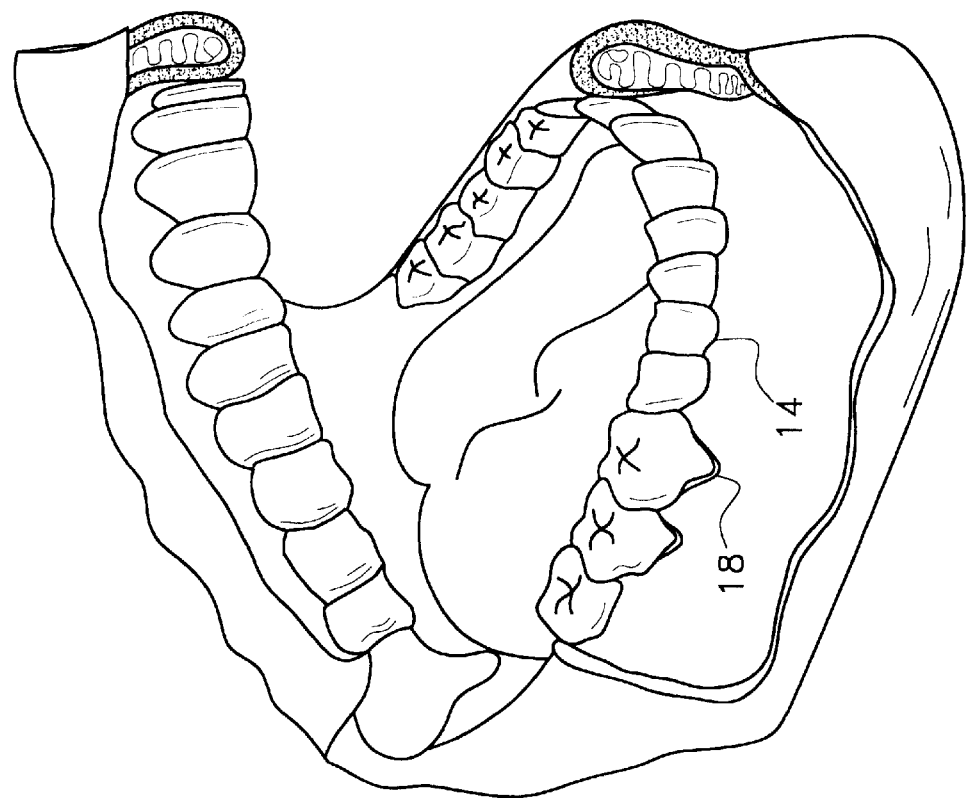

Referring to FIG. 1, a preferred method of applying the present invention composition is illustrated. A periodontal brush 10 is dipped into the composition 12 of the present invention. The brush 10 is then placed against the gum line 14 and the bristles 16 of the brush are advanced into any pockets 18 that may be present on the gum line 14 in between and around the teeth and the gums. As the bristles 16 enter any pocket, the bristles 16 displace any bacteria or food particles that may be present within those pockets 18. Furthermore, the bristles 16 carry the composition 12 of the present invention into those pockets 18. The presence of the melaleuca alternifolia extract oil kills any plaque bacteria that may be left behind in the pocket 18. The melaleuca alternifolia extract oil also kills any new bacteria that enters the pocket 18 for as long as the extract oil is present within that pocket 18.

The coenzyme $Q_{10}$ treats the gum tissue within the pocket 18 on the gum line 14. As such, regeneration of the gum tissue is promoted. The desired effect is to have the gum grow back to the tooth and close the size of the pocket 18 to normal size parameters. After repeated use, the effects of periodontal disease are stopped and then at least partially reversed. If the periodontal disease is not advanced, a near total recovery can be produced. For advanced cases of periodontal disease, the health of the gums can be increased and the tooth loss can be prevented or significantly delayed.

It will be understood that the embodiment of the present invention described and illustrated herein is merely exemplary and a person skilled in the art can make many variations to the embodiment shown without departing from the scope of the present invention. It should also be understood that the various elements from different embodiments can be mixed together to create alternate embodiments that are not specifically described. All such variations, modifications and alternate embodiments are intended to be included within the scope of the present invention as defined by the appended claims.

What is claimed is:

1. A composition for treating pocketing in gums caused by periodontal disease, comprising:

coenzyme $Q_{10}$ being between 0.05% and 75% of said composition by weight;

melaleuca alternifolia extract oil being between 0.02% and 33% of said composition by volume; and a vegetable oil based solution medium into which said coenzyme $Q_{10}$ and said melaleuca alternifolia extract oil are mixed.

2. The composition according to claim 1, wherein said coenzyme $Q_{10}$ is present in a concentration between 200 mg and 1000 mg per ounce.

3. The composition according to claim 1, wherein said melaleuca alternifolia extract oil is present in a concentration between 0.33 ml and 1.5 ml per ounce.

4. A method of treating pockets caused by periodontal disease between and around the teeth and gums, said method comprising the steps of:

preparing a solution containing melaleuca alternifolia extract oil and coenzyme $Q_{10}$;

applying said solution to bristles of a brush;

introducing said solution into said pockets with said bristles, wherein said bristles remove debris from said pockets, said melaleuca alternifolia extract oil kills microbes present in said pockets and said coenzyme $Q_{10}$ promotes the growth of the gums onto the teeth within said pockets.

5. The method according to claim 4, wherein said step of preparing a solution includes producing a solution that contains between 0.05% and 75% of coenzyme $Q_{10}$ by weight.

6. The method according to claim 5, wherein said step of preparing a solution includes producing a solution that contains between 0.02% and 33% of said melaleuca alternifolia extract oil by volume.

7. The method according to claim 4, wherein said step of preparing a solution includes mixing said coenzyme $Q_{10}$ and said antimicrobial agent with a vegetable oil.

* * * * *